United States Patent
Okamoto et al.

(10) Patent No.: US 11,543,419 B2
(45) Date of Patent: Jan. 3, 2023

(54) MEASUREMENT SAMPLE DILUTION LIQUID, KIT, AND MEASUREMENT METHOD

(71) Applicant: TOYOBO CO., LTD., Osaka (JP)

(72) Inventors: Jun Okamoto, Otsu (JP); Keizo Yoneda, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 109 days.

(21) Appl. No.: 16/961,096

(22) PCT Filed: Dec. 27, 2018

(86) PCT No.: PCT/JP2018/048025
§ 371 (c)(1),
(2) Date: Jul. 9, 2020

(87) PCT Pub. No.: WO2019/138899
PCT Pub. Date: Jul. 18, 2019

(65) Prior Publication Data
US 2021/0063417 A1 Mar. 4, 2021

(30) Foreign Application Priority Data
Jan. 11, 2018 (JP) .............................. JP2018-002582

(51) Int. Cl.
*G01N 33/72* (2006.01)
*G01N 1/38* (2006.01)
(Continued)

(52) U.S. Cl.
CPC ............. *G01N 33/721* (2013.01); *G01N 1/38* (2013.01); *G01N 21/29* (2013.01); *G01N 33/538* (2013.01);
(Continued)

(58) Field of Classification Search
CPC ........ G01N 33/721; G01N 1/38; G01N 21/29; G01N 33/538; G01N 33/54388;
(Continued)

(56) References Cited

U.S. PATENT DOCUMENTS 5,610,076 A  3/1997  Founds et al.
2006/0286679 A1  12/2006  Ono et al.
(Continued)

FOREIGN PATENT DOCUMENTS

CN  106814189  6/2017
JP  9-229936 A  9/1997
(Continued)

OTHER PUBLICATIONS

European Search Report dated Oct. 26, 2021 in corresponding European Patent Application No. 18899676.3.
(Continued)

*Primary Examiner* — Jennifer Wecker
*Assistant Examiner* — Michael Paul Shimek
(74) *Attorney, Agent, or Firm* — Wenderoth, Lind & Ponack, L.L.P.

(57) ABSTRACT

Provided are a measurement sample diluent that enables the measurement of the proportion of HbA1c in the total Hb molecules in a measurement sample (HbA1c (%)), with high sensitivity, high accuracy, and high correlation with HPLC without being affected by the length of time required to mix a measurement sample with the measurement sample diluent and to drop the mixture onto an immunochromatographic specimen for measuring HbA1c; and a kit containing the measurement sample diluent. The present invention relates to a measurement sample diluent for immunochromatography for quantifying the proportion of hemoglobin A1c in the total hemoglobin molecules in a measurement sample (hemoglobin A1c (%)); and the measurement sample diluent is
(Continued)

an aqueous solution that contains a non-ionic surfactant, an anionic surfactant, and a buffer.

14 Claims, 1 Drawing Sheet

(51) Int. Cl.
    *G01N 21/29*     (2006.01)
    *G01N 33/538*     (2006.01)
    *G01N 33/548*     (2006.01)
    *G01N 33/543*     (2006.01)

(52) U.S. Cl.
    CPC ..... *G01N 33/548* (2013.01); *G01N 33/54388* (2021.08); *G01N 2001/386* (2013.01)

(58) Field of Classification Search
    CPC ........... G01N 33/548; G01N 2001/386; G01N 33/723; G01N 33/53
    See application file for complete search history.

(56) References Cited

U.S. PATENT DOCUMENTS

| | | | |
|---|---|---|---|
| 2011/0027908 A1 | 2/2011 | Siciliano et al. | |
| 2011/0306150 A1 | 12/2011 | Kato et al. | |
| 2011/0318765 A1* | 12/2011 | Miyazaki | G01N 33/723 |
| | | | 435/7.93 |
| 2012/0309636 A1* | 12/2012 | Gibbons | G06T 7/0012 |
| | | | 506/9 |
| 2015/0024503 A1 | 1/2015 | Taira et al. | |
| 2016/0080548 A1* | 3/2016 | Erickson | H04M 1/72409 |
| | | | 455/556.1 |
| 2016/0334338 A1* | 11/2016 | Ito | G01N 33/723 |
| 2017/0023559 A1 | 1/2017 | Iwamoto et al. | |
| 2017/0045510 A1* | 2/2017 | Ito | G01N 33/723 |
| 2018/0209970 A1 | 7/2018 | Kato et al. | |
| 2018/0299455 A1 | 10/2018 | Kawaminami et al. | |
| 2019/0353651 A1 | 11/2019 | Kato et al. | |

FOREIGN PATENT DOCUMENTS

| | | |
|---|---|---|
| JP | 2006-266811 A | 10/2006 |
| JP | 2012-251789 A | 12/2012 |
| JP | 2015-1398 A | 1/2015 |
| JP | 2015-158515 A | 9/2015 |
| JP | 2015-200517 A | 11/2015 |
| JP | 2016-161329 A | 9/2016 |
| WO | 2004/106930 A1 | 12/2004 |
| WO | 2017/010574 A1 | 1/2017 |
| WO | 2017/065213 A1 | 4/2017 |
| WO | 2017/094825 A1 | 6/2017 |
| WO | 2017/126593 A1 | 7/2017 |

OTHER PUBLICATIONS

International Search Report dated Apr. 9, 2019, issued in counterpart International Application No. PCT/JP2018/048025. (2 pages).

* cited by examiner

MEASUREMENT SAMPLE DILUTION LIQUID, KIT, AND MEASUREMENT METHOD

TECHNICAL FIELD

The present invention relates to a method for measuring the proportion of hemoglobin A1c in the total hemoglobin molecules (hemoglobin A1c (%)) in a measurement sample by using immunochromatography, a measurement sample diluent for use in the measurement method, and a kit containing the measurement sample diluent.

BACKGROUND ART

The International Diabetes Federation reports that the number of people with diabetes has been rapidly increasing throughout the world. This includes developing countries such as China, India, and Brazil, as well as developed countries such as the United States and European countries. There were about 420 million diabetes patients in 2015, and this number is expected to reach about 640 million patients by 2040, increasing the importance of diabetes diagnosis.

Glycated hemoglobin molecules are formed by modification of hemoglobin ("Hb" below), which carries oxygen in blood, with attachment of a sugar (glucose). Among these glycated hemoglobin molecules, hemoglobin A1c ("HbA1c" below) is one of the diabetes diagnosis indicators, and refers to a form of hemoglobin in which the N-terminal valine residue of its β chain is glycated. HbA1c (%), which is the proportion of HbA1c in the total Hb level, reflects the average blood sugar level over the past 1 to 2 months, and is thus used in monitoring the long-term progress of diabetes.

HbA1c (%) has been measured by using a measurement technique, such as HPLC, capillary electrophoresis, enzymatic colorimetry, or immunonephelometry. However, due to the requirements of specialized knowledge, as well as large, expensive analysis equipment, these measurement methods are mainly used in large hospitals and laboratories that perform a large number of tests; there is no simple method for measuring HbA1c (%) that can be used in small hospitals.

The term "POCT" has been attracting attention in medical settings. POCT stands for "Point Of Care Testing," which refers to a clinical test performed by a health care professional adjacent to a subject. POCT is becoming common in the diagnosis of diabetes because it offers test results instantly and on the spot, unlike clinical tests performed in the central laboratories of large hospitals.

Among such POCT for the purpose of measuring HbA1c (%), there is proposed a technique using immunochromatography. Immunochromatography is an immunoassay that uses capillary action, and has been widely used in pregnancy and influenza testing worldwide. Although visual judgement (qualitative evaluation) is generally used in conventional immunochromatography, recent years have seen increasing development of techniques for quantifying the amount of an analyte contained in a measurement sample, using analysis equipment such as an immunochromatographic reader.

An example of techniques for quantifying the amount of an analyte using immunochromatography is a sandwich assay using antigen-antibody reaction. The sandwich assay uses two types of antibodies for which the epitope of the analyte is different. One antibody is used as a detection antibody sensitized with detection particles, such as colloidal gold, colored latex particles, and fluorescent particles. The other antibody forms a test line as a linearly immobilized capture antibody on the surface of a porous support. Additionally, another antibody that specifically captures the detection antibody is linearly immobilized in the form of a control line at a position different from the position of the test line on the surface of the porous support. The analyte contained in a measurement sample starts to develop at one end of the porous support (upstream), and migrates while forming an immunocomplex with the detection antibody. The analyte then comes into contact with the capture antibody on the test line; and is captured, thereby producing a color. Free detection reagent molecules that did not form an immunocomplex with the analyte pass through the test line; and are captured by the antibody of the control line, thereby producing a color. The amount of the analyte can be quantified based on the color intensity, using equipment such as an immunochromatographic reader.

As stated above, measurement of HbA1c (%) by immunochromatography uses an antibody specific to the glycation site of HbA1c (the N-terminal valine residue of the β chain of Hb). However, it is known that the glycation site is buried in Hb rather than on the surface of Hb, and is present in an area where the antibody cannot easily bind to the glycation site under physiological conditions. Because of this nature, studies report techniques of exposing the glycation site on the surface of Hb ("denaturation" below) in order to measure HbA1c (%) by efficiently reacting an antibody that recognizes the glycation site as an epitope.

PTL 1 and PTL 2 disclose a configuration in which a measurement sample diluent contains a surfactant, and an immunochromatographic specimen is loaded with a cyclic polysaccharide. This invention is expected to provide some effect in terms of avoiding interference of the downstream antigen-antibody reaction, and exposing the epitope (i.e., improvement in measurement sensitivity). However, due to uneven development caused downstream in this invention, measurement accuracy is insufficient. Additionally, because a measurement sample would be manually diluted using an immunochromatography kit in actuality, the length of time required to mix a measurement sample with a measurement sample diluent and then to drop the mixture onto an immunochromatographic specimen would clearly vary between individuals ("mixing time" below). However, this invention does not select the reaction rate at which the epitope is exposed in the measurement sample diluent (i.e., a surfactant, taking into consideration the variations in measurement results caused by the mixing time); thus, measurement accuracy would further decrease depending on operators. Additionally, due to the use of colloidal gold or latex particles as detection particles, the invention would also be unsatisfactory in terms of sensitivity, accuracy, and correlation with HPLC. In this invention, the optimum formulation of the measurement sample diluent is described as varying depending on the detection particles for use; however, cellulose particles are not mentioned.

PTL 3 and PTL 4 disclose a configuration in which a measurement sample diluent contains a non-ionic surfactant, and an immunochromatographic specimen is loaded with an anionic surfactant. This invention is expected to provide some effect in terms of improving uneven development. However, the surfactant supported on the immunochromatographic specimen is unable to expose the epitope on the surface of Hb over the very short period of time during which a diluted measurement sample develops. Thus, this invention is insufficient in measurement sensitivity, and is greatly affected by the mixing time. Moreover, due to the use of colloidal gold as detection particles, the invention is unsatisfactory in terms of sensitivity, accuracy, and correlation with HPLC.

CITATION LIST

Patent Literature

PTL 1: JP2012-251789A
PTL 2: JP2015-158515A
PTL 3: JP2015-200517A
PTL 4: JP2016-161329A

SUMMARY OF INVENTION

Technical Problem

In view of the problems described above, an object of the present invention is to provide a method for measuring the proportion of HbA1c in the total Hb molecules (HbA1c (%)) in a measurement sample by immunochromatography, with higher sensitivity, accuracy, and correlation with HPLC than in related art; a measurement sample diluent for use in the measurement method; and a kit containing the measurement sample diluent. More specifically, an object of the present invention is to provide a method for measuring the proportion of HbA1c in the total Hb molecules (HbA1c (%)) in a measurement sample that is less likely, as compared with the related art, to be affected by the length of time required to mix a measurement sample with a measurement sample diluent and to drop the mixture onto an immunochromatographic specimen for measuring HbA1c; to provide a measurement sample diluent for use in the measurement method; and to provide a kit containing the measurement sample diluent.

Solution to Problem

The present inventors conducted extensive research to solve the problems. They found that the use of an aqueous solution containing at least a non-ionic surfactant, an anionic surfactant, and a buffer as a measurement sample diluent substantially increases the sensitivity, accuracy, and correlation with HPLC of immunochromatography, as compared with the related art; and prevents immunochromatography from being affected by the length of time required to mix a measurement sample with a measurement sample diluent and to drop the mixture onto an immunochromatographic specimen. The inventors also found that the use of an aqueous solution that contains an oxidation agent and/or an azidation agent in addition to the measurement sample diluent further increases the sensitivity, accuracy, and correlation with HPLC; and then completed the present invention. The measurement sample diluent according to the present invention is particularly useful when the detection particles are cellulose particles.

Specifically, typical subject matter of the present invention is as described below.

Item 1.
A measurement sample diluent for immunochromatography for quantifying hemoglobin A1c (%), which is the proportion of hemoglobin A1c in the total hemoglobin molecules in a measurement sample, the measurement sample diluent being an aqueous solution comprising
an anionic surfactant,
a non-ionic surfactant, and
a buffer.

Item 2.
The measurement sample diluent according to Item 1, wherein the anionic surfactant is an alkyl sulfate.

Item 3.
The measurement sample diluent according to Item 1 or 2, wherein the non-ionic surfactant is a polyoxyethylene sorbitan fatty acid ester.

Item 4.
The measurement sample diluent according to Item 1 or 2, wherein the non-ionic surfactant is a mixture of a polyoxyethylene sorbitan fatty acid ester and a polyoxyethylene alkyl phenyl ether.

Item 5.
The measurement sample diluent according to any one of Items 1 to 4, comprising the anionic surfactant in an amount of 0.05 to 2.0 wt %, and the non-ionic surfactant in an amount of 0.05 to 3.0 wt %.

Item 6.
The measurement sample diluent according to any one of Items 1 to 5, further comprising an oxidation agent.

Item 7.
The measurement sample diluent according to Item 6, wherein the oxidation agent is nitrite.

Item 8.
The measurement sample diluent according to any one of Items 1 to 7, further comprising an azidation agent.

Item 9.
The measurement sample diluent according to Item 8, wherein the azidation agent is sodium azide.

Item 10.
A measurement kit for quantifying the proportion of hemoglobin A1c in the total hemoglobin molecules, the measurement kit comprising
the measurement sample diluent of any one of Items 1 to 9,
an immunochromatographic specimen, and
an immunochromatographic reader.

Item 11.
The measurement kit according to Item 10, wherein the immunochromatographic specimen comprises
(1) a sample pad,
(2) a conjugate pad loaded with a complex of an antibody for capturing any hemoglobin or hemoglobin A1c in the measurement sample and a cellulose particle,
(3) a membrane on which an antibody for specifically capturing any hemoglobin or hemoglobin A1c in the measurement sample is linearly immobilized, and
(4) an absorbent pad.

Item 12.
A method for quantifying the proportion of hemoglobin A1c in the total hemoglobin molecules in a measurement sample, using the measurement sample diluent or the measurement kit of any one of Items 1 to 11, the method comprising performing at least the following steps (i) to (iii) in this order:
step (i): mixing the measurement sample and the measurement sample diluent in a volume ratio of 1:49 to 1:999 to dilute the measurement sample;
step (ii): dropping the mixture of step (i) onto a sample pad on an immunochromatographic specimen; and
step (iii): determining by colorimetry the proportion of hemoglobin A1c in the total hemoglobin molecules based on reflection absorption of a test line and reflection absorption of a control line on the immunochromatographic specimen.

Item 13.

The method according to Item 12, wherein the measurement sample and the measurement sample diluent are mixed in a volume ratio of 1:99 to 1:499 to dilute the measurement sample.

Advantageous Effects of Invention

Because the measurement sample diluent according to the present invention is an aqueous solution containing a non-ionic surfactant, an anionic surfactant, and a buffer, the diluent enables the measurement of the proportion of HbA1c in the total Hb molecules (HbA1c (%)) in a measurement sample, with high sensitivity, high accuracy, and high correlation with HPLC, without being affected by the length of time required to mix a measurement sample with the measurement sample diluent and to drop the mixture onto an immunochromatographic specimen.

DESCRIPTION OF EMBODIMENTS

In the present invention, examples of measurement samples include, although not particularly limited to, biological samples, such as blood, lymph, spinal fluid, sweat, urine, lachrymal fluid, saliva, skin, mucosa, and hair. The blood for use in samples may not only be whole blood, but also serum, blood cells, or plasma obtained by centrifuging blood. Additionally, the measurement sample is not limited to those of human origin; and may also be biological samples originated from mammals, such as dogs, cats, and cows. The item to be measured in the present invention is the proportion of HbA1c in the total Hb molecules (HbA1c (%)) in a measurement sample.

The measurement sample diluent according to the present invention is an aqueous solution containing at least a non-ionic surfactant, an anionic surfactant, and a buffer. Due to the presence of an anionic surfactant in the measurement sample diluent, the diluent can reduce variations in measurement value (e.g., reflection absorption of the test line, described later) caused by the different lengths of time required to mix a measurement sample with the measurement sample diluent and to drop the mixture onto an immunochromatographic specimen; and can also increase measurement sensitivity and measurement accuracy. Additionally, due to the presence of a non-ionic surfactant in the measurement sample diluent, the diluent can reduce uneven development of the measurement sample that migrates (flows) on the immunochromatographic specimen, thus increasing measurement accuracy. The absence of a buffer may interfere with downstream antigen-antibody reaction depending on the pH of the measurement sample, thus decreasing measurement sensitivity. The item to be measured in the present invention is the proportion of HbA1c in the total Hb molecules (HbA1c (%)) in a measurement sample; thus, either the non-ionic surfactant or the anionic surfactant must be a surfactant that exhibits hemolytic activity.

The anionic surfactant can be any anionic surfactant that can instantly denature HbA1c in a measurement sample without interfering with downstream antigen-antibody reaction. Examples of anionic surfactants include alkyl sulfates, such as sodium dodecyl sulfate (SDS), and lithium dodecyl sulfate (LDS); bile salts, such as sodium cholate, and sodium deoxycholate; polyoxyethylene alkyl ether sulfates, such as sodium polyoxyethylene lauryl ether sulfate; alkylbenzene sulfonates, such as sodium dodecylbenzenesulfonate; acyl amino acid salts, such as lauroyl methylalanine, and N-lauroylsarcosine sodium salt; sodium dialkylsulfosuccinate, sodium β-naphthalene sulfonate formalin condensate, and special polycarboxylic acid-based polymeric surfactants. Of these, alkyl sulfates are preferable, and sodium dodecyl sulfate (SDS) is more preferable. Alkyl sulfate are surfactants that exhibit hemolytic activity.

In the present invention, the concentration of the anionic surfactant in the measurement sample diluent is, although not particularly limited to, preferably 0.05 to 2.0 wt %, and more preferably 0.1 to 1.0 wt %. When the concentration is low, the denaturation of HbA1c takes time; thus, the measurement value (e.g., reflection absorption of the test line, described later) may vary depending on the length of time required to mix the measurement sample with the measurement sample diluent and to drop the mixture onto an immunochromatographic specimen, decreasing measurement sensitivity and measurement accuracy. A high concentration, on the other hand, may interfere with downstream antigen-antibody reaction, leading to decreased measurement sensitivity.

In the present invention, the non-ionic surfactant can be any non-ionic surfactant that has an action of facilitating downstream antigen-antibody reaction, while increasing the uniformity of development of the measurement sample. Examples of non-ionic surfactants include polyoxyethylene alkyl phenyl ether (e.g., Triton, registered trademark), polyoxyethylene alkyl ether (e.g., Brij, registered trademark), polyoxyethylene sorbitan fatty acid ester (e.g., Tween, registered trademark), polyoxyethylene fatty acid ester (e.g., Emanon, registered trademark), polyoxyethylene alkyl amine (e.g., Amiet, registered trademark), polyoxyethylene sorbitol fatty acid ester (e.g., Rheodol, registered trademark), sorbitan fatty acid ester (e.g., Rheodol, registered trademark), glycerol fatty acid ester (e.g., Rheodol, registered trademark), alkyl alkanolamide (e.g., Aminon, registered trademark), alkyl imidazoline (e.g., Homogenol, registered trademark), and sucrose fatty acid ester. Of these, from the standpoint of uniform development of the measurement sample, polyoxyethylene sorbitan fatty acid esters (e.g., Tween, registered trademark) are preferable; and from the standpoint of facilitating downstream antigen-antibody reaction, polyoxyethylene alkyl phenyl ethers (e.g., Triton, registered trademark and the like) are preferable. More preferably, the measurement sample diluent contains both a polyoxyethylene sorbitan fatty acid ester (e.g., Tween, registered trademark) and a polyoxyethylene alkyl phenyl ether (e.g., Triton, registered trademark). Commercially available polyoxyethylene sorbitan fatty acid esters (e.g., Tween, registered trademark) for use are preferably, for example, Tween (registered trademark) 20, Tween (registered trademark) 40, Tween (registered trademark) 60, and Tween (registered trademark) 80 (produced by Wako Pure Chemical Industries, Ltd.). Commercially available polyoxyethylene alkyl phenyl ethers (e.g., Triton, registered trademark) for use are preferably, for example, Triton X (registered trademark) 100, Triton X (registered trademark) 114, and Nonidet (registered trademark) P-40 (produced by Wako Pure Chemical Industries, Ltd.). While polyoxyethylene sorbitan fatty acid esters (e.g., Tween, registered trademark)

have poor hemolytic activity, polyoxyethylene alkyl phenyl ethers (e.g., Triton, registered trademark) are surfactants that exhibit hemolytic activity.

In the present invention, the concentration of the non-ionic surfactant in the measurement sample diluent is preferably 0.05 to 3.0 wt %. When the non-ionic surfactant for use is a mixture of a polyoxyethylene sorbitan fatty acid ester (e.g., Tween, registered trademark) and a polyoxyethylene alkyl phenyl ether (e.g., Triton, registered trademark), the concentration of the polyoxyethylene sorbitan fatty acid ester is preferably 0.05 to 3.0 wt %, and more preferably 0.1 to 2.0 wt %. A low concentration thereof may make it difficult for the diluent to develop downstream; or make the development non-uniform, substantially decreasing measurement accuracy. A high concentration thereof, on the other hand, may allow the physically adsorbed detection particles to become detached from the detection antibody and/or allow the membrane to become detached from the capture antibody, leading to a failure to obtain a measurement value, or substantially decreasing measurement sensitivity when a measurement value is even obtained. The concentration of the polyoxyethylene alkyl phenyl ether is preferably 0.1 to 2.0 wt %, and more preferably 0.1 to 1.0 wt %. A low concentration thereof may lead to a failure to obtain an effect of facilitating downstream antigen-antibody reaction, decreasing measurement sensitivity. A high concentration thereof, on the other hand, may allow the physically adsorbed detection particles to become detached from the detection antibody and/or allow the membrane to become detached from the capture antibody, leading to an absolute failure to obtain a measurement value, or substantially decreasing measurement sensitivity when a measurement value is even obtained.

In the present invention, the buffer for use may be any buffer that has a sufficient buffering capacity within a target pH range. Examples include tris, phosphoric acid, phthalic acid, citric acid, maleic acid, succinic acid, oxalic acid, boric acid, tartaric acid, acetic acid, carbonic acid, and Good's buffers (MES, ADA, PIPES, ACES, cholamine chloride hydrochloride, BES, TES, HEPES, acetamidoglycine, tricine, glycine amide, bicine). Of these, tris, phosphoric acid, MES, PIPES, TES, and HEPES are preferable; and tris, phosphoric acid, and PIPES are more preferable, for example, because these buffers have a sufficient buffering capacity at around a pH of 7.0, which falls within the optimum pH range for the antibodies used in the present invention. The concentration of the buffer can be any concentration at which the buffer can have a sufficient buffering capacity within a target pH range, and is preferably about 10 to 100 mM.

In the present invention, the measurement sample diluent may contain an oxidation agent, in addition to the non-ionic surfactant, the anionic surfactant, and the buffer. The oxidation agent can be any oxidation agent that oxidizes Hb, and that does not interfere with downstream antigen-antibody reaction. Examples include halogen oxoacid salts, salts of transition metal complexes, peroxides, permanganates, chromates, nitrites, and superoxides. Examples of halogen oxoacid salts include alkali metal salts, alkaline earth metal salts, and ammonium salts of hypochlorous acid, chlorous acid, chloric acid, perchloric acid, hypobromous acid, bromous acid, bromic acid, perbromic acid, hypoiodous acid, iodous acid, iodic acid, or periodic acid. Examples of salts of transition metal complexes include ferricyanates of alkali metal salts, alkaline earth metal salts, or ammonium salts. Example of peroxides include organic peroxides. Examples of permanganates include permanganates of alkali metals or alkaline earth metals. Of these, nitrites are preferable, and sodium nitrite is more preferable. The presence of an oxidation agent helps to reduce uneven antigen-antibody reaction caused by uneven oxidation of Hb in a measurement sample, and can thus increase measurement accuracy. The oxidation agent also oxidizes substances that cause non-specific reaction in the measurement sample; and can thus restrain the progress of non-specific reaction, increasing measurement accuracy.

In the present invention, the concentration of the oxidation agent in the measurement sample diluent is, although not particularly limited to, preferably 0.01 to 1.0 wt %. A low concentration may result in insufficient oxidation of Hb and variations of the measurement value (e.g., reflection absorption of the test line, described later), lowering measurement accuracy. A high concentration, on the other hand, may interfere with downstream antigen-antibody reaction, lowering measurement sensitivity.

The measurement sample diluent according to the present invention may contain an azidation agent in addition to the non-ionic surfactant, the anionic surfactant, and the buffer. The azidation agent can be any azidation agent that can change Hb to its azide form, and that does not interfere with downstream antigen-antibody reaction. The azidation agent is preferably sodium azide. The azidation agent also acts as an antiseptic in storage. The presence of an azidation agent helps to reduce uneven antigen-antibody reaction caused by uneven azidation of Hb in a measurement sample, and can thus increase measurement accuracy. The azidation agent also changes substances that may cause non-specific reaction in the measurement sample into their azide forms to thereby restrain the progress of non-specific reaction, and can thus increase measurement accuracy.

The concentration of the azidation agent can be any concentration, and is preferably 0.01 to 0.1 wt %. A low concentration may result in insufficient azidation of Hb and variations of the measurement value (e.g., reflection absorption of the test line, described later), lowering measurement accuracy. A high concentration, on the other hand, may interfere with downstream antigen-antibody reaction, lowering measurement sensitivity. Additionally, a sodium azide concentration of 0.1 wt % or more is not preferable because of its toxicity.

The measurement sample diluent according to the present invention may optionally contain a blocking protein (e.g., blocking peptide fragment (BPF), bovine serum albumin (BSA), and casein), a salt (e.g., sodium chloride, potassium chloride, calcium chloride, magnesium chloride, and aluminum chloride), and/or an antibody stabilizer (e.g., monosaccharides, oligosaccharides, polysaccharides, sugar alcohols, glycerol, gluconate, amino acids, albumins, globulins, and fibrous proteins).

The dilution ratio of a measurement sample with the measurement sample diluent can be any ratio; and is preferably 50- to 1000-fold, and more preferably 100- to 500-fold. A small dilution ratio of the measurement sample may make it difficult for the sample to develop downstream. Additionally, the sample may become susceptible to foreign substances in the measurement sample, lowering measurement accuracy. A high dilution ratio of the measurement sample, on the other hand, decreases the concentration of Hb and HbA1c in a measurement sample, possibly lowering measurement sensitivity.

In the present invention, the immunochromatography measurement kit contains an immunochromatographic specimen and an immunochromatographic reader, in addition to the measurement sample diluent.

Figure 1:
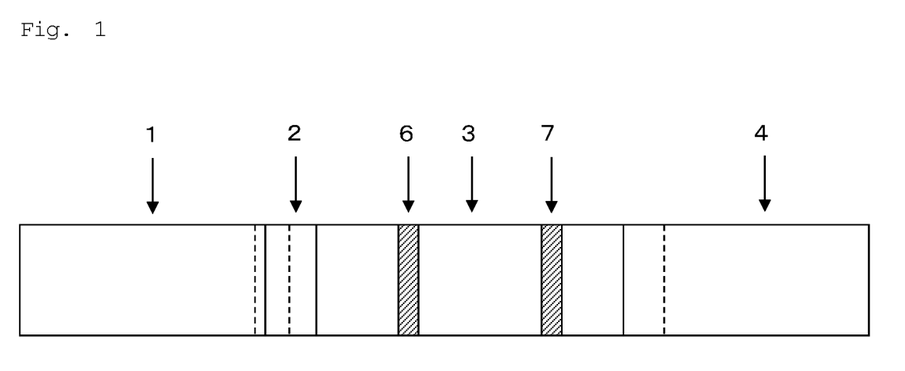
FIG. 1 illustrates an example of immunochromatographic specimens for use in the present invention (top view).
Figure 2:
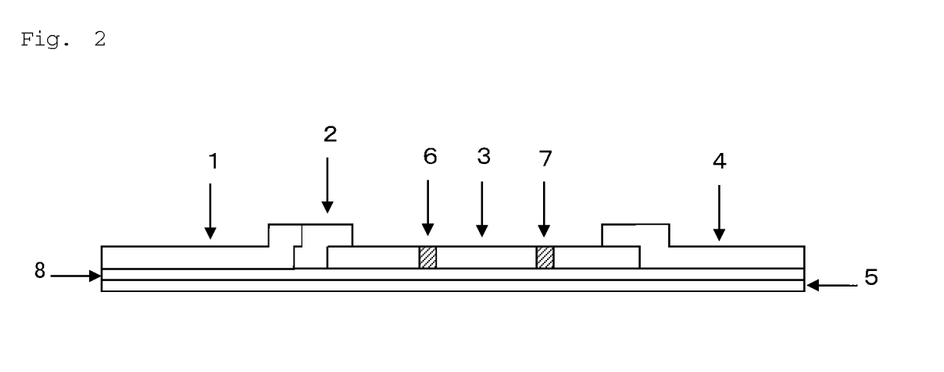
FIG. 2 illustrates an example of immunochromatographic specimens for use in the present invention (side view).

In the present invention, the configuration of the immunochromatographic specimen can be any configuration; however, it is preferably configured such that with a measurement sample solution adding zone (dropping zone) of the immunochromatographic specimen positioned upstream, a sample pad having the adding zone, a conjugate pad, a membrane, and an absorbent pad are continuously arranged. Below, an example of immunochromatographic specimens of the present invention is explained with reference to drawings. However, the example in no way restricts the present invention. In FIGS. 1 and 2, reference numeral 1 indicates a sample pad, reference numeral 2 indicates a conjugate pad, reference numeral 3 indicates a membrane, reference numeral 4 indicates an absorbent pad, reference numeral 5 indicates a backing sheet, reference numeral 6 indicates a test line, reference numeral 7 indicates a control line, and reference numeral 8 indicates an adhesive sheet.

In the example illustrated in FIGS. 1 and 2, the immunochromatographic specimen has an elongated strip-like shape with a width of 3 to 5 mm (preferably about 4 mm), and a length of 40 to 100 mm (preferably about 60 mm). Test line 6, which is a linearly immobilized capture antibody, is formed at about 15 mm from the upstream end of membrane 3 of the immunochromatographic test specimen. Control line 7, which is another linearly immobilized capture antibody, is formed at about 20 mm from the upstream end of membrane 3. Additionally, conjugation pad 2 of the immunochromatographic specimen is loaded with a test line detection reagent, which is a complex of a detection antibody and a detection particle; and a control line detection reagent, which is a complex of a labeled blocking protein and a detection particle.

The material of sample pad 1 can be any material that is capable of rapidly absorbing the measurement sample and then allowing the sample to develop toward the downstream conjugate pad, membrane, and absorbent pad. Examples of materials include cellulose filter paper, cellulose non-woven fabric, glass filter paper, glass non-woven fabric, polyester filter paper, polyester non-woven fabric, polyethylene filter paper, and polyethylene non-woven fabric. Of these, cellulose filter paper is preferable. Sample pad 1 preferably has a thickness of 0.1 to 2.0 mm, and more preferably 0.2 to 1.0 mm. A low thickness may lead to a non-uniform flow of the measurement sample downstream, lowering measurement accuracy. A high thickness, on the other hand, may lead to delayed development downstream, increasing the measurement time. Additionally, a greater amount of the measurement sample may be necessary for the development of the sample downstream.

The material of conjugate pad 2 can be any material that is capable of retaining the test line detection reagent and the control line detection reagent in their dry form, and rapidly releasing both detection reagents according to development of the measurement sample downstream. Examples of materials include cellulose filter paper, cellulose non-woven fabric, glass filter paper, glass non-woven fabric, polyester filter paper, polyester non-woven fabric, polyethylene filter paper, and polyethylene non-woven fabric. Of these, glass filter paper is preferable. Conjugate pad 2 preferably has a thickness of 0.1 to 2.0 mm, and more preferably 0.2 to 1.0 mm. A low thickness may lead to a failure to retain a target amount of the test line detection reagent and the control line detection reagent in their dry form. A high thickness, on the other hand, may lead to delayed development downstream, increasing the measurement time. Additionally, a greater amount of the measurement sample may be necessary for the development of the sample downstream.

The material of membrane 3 can be any material that is capable of allowing the measurement sample to accurately and uniformly develop. Examples of materials include a membrane made of cellulose, cellulose derivatives, nitrocellulose, cellulose acetate, polyurethane, polyester, polyethylene, polyvinyl chloride, polyvinylidene fluoride, or nylon. Of these, a membrane made of nitrocellulose is preferable.

The material of absorbent pad 4 can be any material that is capable of rapidly absorbing the measurement sample that has developed from upstream, and retaining the sample to prevent the sample from flowing backward. Examples of materials include cellulose filter paper, cellulose non-woven fabric, glass filter paper, glass non-woven fabric, polyester filter paper, polyester non-woven fabric, polyethylene filter paper, and polyethylene non-woven fabric. Of these, cellulose filter paper is preferable. Absorbent pad 4 preferably has a thickness of 0.2 to 5.0 mm, and more preferably 0.5 to 2.0 mm. A low thickness may allow the measurement sample that has been absorbed by the absorbent pad to backflow toward the membrane, depending on the amount of the dropped measurement sample. A high thickness is not preferable from the standpoint of POCT, due to an increased size of the immunochromatographic specimen and an increased size of a housing case that covers the immunochromatographic specimen.

The test line detection reagent loaded on conjugate pad 2 can be any detection reagent, and is preferably a complex of a detection antibody and a detection particle.

The detection antibody is, although not particularly limited to, preferably anti-Hb antibody or anti-HbA1c antibody, and more preferably anti-HbA1c antibody. The anti-Hb antibody and anti-HbA1c antibody for use may be a commercially available product, or may be separately produced in accordance with a known method. The detection antibody may be a monoclonal antibody or a polyclonal antibody, and may have any molecular size.

The detection particles can be any detection particles, and the detection particles for use may be colored particles or fluorescent particles. Examples of colored particles include metal particles, latex particles, and cellulose particles. Examples of metal particles include colloidal gold, colloidal silver, platinum colloids, palladium colloids, gold nanorods, gold nanoplates, and silver nanoplates. The metal particles preferably have a mean particle size of 1 to 100 nm. Examples of latex particles include those formed of, for example, polystyrene, polymethylmethacrylate, or an acrylic acid polymer. The latex particles preferably have a mean particle size of 25 to 500 nm. Examples of fluorescent particles include those formed of, for example, polystyrene, polymethylmethacrylate, polyvinyl toluene, or silica. Examples of fluorescent dyes include fluorescein, and derivatives thereof; rhodamine, and derivatives thereof; and cyanine, and derivatives thereof. Of these, cellulose particles are preferable due to their high dispersibility and excellent visibility. Below, cellulose particles are described in detail.

Due to the presence of numerous hydroxyl groups, the cellulose particles are capable of not only retaining a larger amount of a reactive dye through covalent bonds, but also maintaining stable dispersibility in water after deep-dying. The cellulose particles for use may be, for example, regenerated cellulose, purified cellulose, or natural cellulose; or may be partially derivatized cellulose. Preferably 20 to 90 wt %, more preferably 20 to 80 wt %, and still more preferably 20 to 70 wt % of the cellulose particles is derived from cellulose on a weight basis.

The mean particle size of the cellulose particles can be any size, and is preferably 100 to 1000 nm, and more preferably 200 to 800 nm. A mean particle size of more than 1000 nm may lead to delayed development downstream, increasing the measurement time. Additionally, the detection particles may easily become captured on the membrane, allowing the background to produce a color, and thus making color development on the test line and the control line unclear. A mean particle size of less than 100 nm, on the other hand, may decrease the amount of antibodies capable of physical adsorption or chemical bond, decreasing measurement sensitivity.

The color of the cellulose particles can be any color. Examples of colors of the cellulose particles include red, blue, yellow, green, black, white, and fluorescent colors. Of these, blue and black, which are less affected by the red color derived from Hb in the background, are preferable, and blue is more preferable. Such cellulose particles include colored cellulose nanobeads (NanoAct, registered trademark, produced by Asahi Kasei Corporation); of these, navy (BL1), dark navy (BL2), and black (KR1) are preferable, and navy (BL1) and dark navy (BL2) are more preferable.

The test line detection reagent is preferably blocked by a blocking protein. The blocking protein is, although not particularly limited to, preferably a blocking peptide fragment ("BPF" below), which is a protein of microbial origin; and bovine serum albumin ("BSA" below) and casein, which are proteins of animal origin, with the microorganism-originated protein BPF being more preferable. Due to its smaller molecular weight (about 22 kDa) than BSA (about 66 kDa), BPF enables measurement with higher accuracy. BSA poses a risk of contamination caused by foreign substances due to its origin from cows; however, BPF has no such risk due to its microbial origin. Dissolving casein requires the use of an alkaline boric acid buffer (pH=8.5 to 10), which may lead to inactivation of antibodies, thus lowering sensitivity. The boric acid buffer also involves a high environmental risk. However, BPF can be dissolved in Tris, phosphoric acid, PIPES, etc. in a neutral pH range, and is thus preferable. The blocking protein for use may be a commercially available product, or may be separately produced in accordance with a known method. The blocking protein may have any molecular size, and preferably has an average molecular weight of 100 kDa or less. Typically, the smaller the molecular size of the blocking protein, the higher the binding amount of the blocking protein per detection particle. Thus, a blocking protein with a smaller molecular size contributes to increasing measurement accuracy.

The method for binding the detection antibody with cellulose particles can be any method. However, it is preferable to perform sensitization by physical adsorption through hydrophobic bond, or by chemical bond through covalent bond. Due to its simple operation and low cost, physical adsorption is more preferable. In order to increase sensitization efficiency, a reactive active group may be introduced into cellulose particles. The reactive active group can be any reactive active group. Examples include carboxyl groups, amino groups, aldehyde groups, thiol groups, epoxy groups, and hydroxyl groups. Of these, carboxyl groups and amino groups are preferable. An introduced carboxyl group can form a covalent bond with the amino group of a ligand when a carbodiimide is used.

The control line detection reagent loaded on conjugate pad 2 for use in the present invention is, although not particularly limited to, preferably a complex of a labeled blocking protein and detection particles.

The detection particles of the test line detection reagent and the detection particles of the control line detection reagent preferably have substantially the same mean particle size. The phrase "substantially the same" as used here means that the difference in mean particle size between the detection particles of the test line detection reagent and the detection particles of the control line detection reagent falls within ±50 nm. A different mean particle size between them may cause a difference in downstream development rate and color intensity, rendering the control line unable to correct the test line, and thus decreasing measurement accuracy.

The detection particles of the test line detection reagent and the detection particles of the control line detection reagent preferably have substantially the same color. The phrase "substantially the same" as used here means that the difference in maximum absorption wavelength between the detection particles of the test line detection reagent and the detection particles of the control line detection reagent falls within ±20 nm. A different color between them requires, for example, multiple LED-PD combinations that correspond to respective colors of the test line and the control line, when measurement is performed with a typical light-emitting diode ("LED" below)-photodiode ("PD" below) measurement device; thus, the size of the device is increased.

The labelling substance in the labeled blocking protein can be any substance. From the standpoint of, for example, relatively low cost, availability, and a proven record in the protein labelling field, biotin or digoxigenin is preferable; and biotin is more preferable.

The method for labeling the blocking protein can be any method, and is preferably a method capable of forming a covalent bond through chemical reaction. Examples include an N-hydroxysuccinimide method. The use of the N-hydroxysuccinimide method, for example, enables selective activation of the carboxyl group of biotin through condensation reaction with an N-hydroxylamine compound in the presence of a dehydrating condensation agent; and labels the amino group of the blocking protein with the carboxyl group through an amide bond. The N-hydroxylamine compound for use in the condensation reaction can be any N-hydroxylamine compound. Examples include N-hydroxysuccinimide, N-hydroxynorbornene-2,3-imidodicarboxylic acid, 2-hydroxyimino-2-cyanoacetic acid ethyl ester, 2-hydroxyimino-2-cyanoacetamide, N-hydroxypiperidine, N-hydroxyphthalimide, N-hydroxyimidazole, and N-hydroxymaleimide. These compounds may be used in a combination of two or more. Of these, N-hydroxysuccinimide ("NHS" below) is preferable from the standpoint of, for example, relatively low cost, availability, and a proven record in the peptide synthesis field. The dehydrating condensation agent for use in the condensation reaction may be any dehydrating condensation agent. Examples include 1-ethyl-3-dimethylaminopropylcarbodiimide hydrochloride, and 1-cyclohexyl-(2-morphonyl-4-ethyl)-carbodiimide metho-p-toluenesulfonate. Of these, 1-ethyl-3-dimethylaminopropylcarbodiimide hydrochloride ("EDC" below) is preferable from the standpoint of a proven record as a general-purpose water-soluble condensation agent, for example, in the peptide synthesis field. The reaction temperature is, although not particularly limited to, preferably 10 to 50° C., and more preferably 20 to 40° C. The reaction time varies depending on the reaction temperature, and is typically 5 minutes to 24 hours. The unreacted N-hydroxylamine compound and dehydrating condensation agent contained in the reaction solution can be easily separated from the aqueous solvent through filtration or centrifugation.

The blocking protein of the labeled blocking protein is, although not particularly limited to, preferably a blocking peptide fragment ("BPF" below), which is a protein of microbial origin; and bovine serum albumin ("BSA" below) and casein, which are proteins of animal origin, with the microorganism-originated BPF being more preferable. Due to its smaller molecular weight (about 22 kDa) than BSA (about 66 kDa), BPF enables measurement with higher sensitivity. BSA poses a risk of contamination caused by foreign substances due to its origin from cows; however, BPF has no such risk due to its microbial origin. Dissolving casein requires the use of an alkaline boric acid buffer (pH=8.5 to 10), and the boric acid buffer involves a high environmental risk. However, BPF can be dissolved in Tris, phosphoric acid, PIPES, etc. in a neutral pH range, and is thus preferable. The blocking protein for use may be a commercially available product, or may be separately produced in accordance with a known method. The blocking protein may have any molecular size, and preferably has an average molecular weight of 100 kDa or less. Typically, the smaller the molecular size of the blocking protein, the higher the binding amount of the blocking protein per detection particle. Thus, a blocking protein with a smaller molecular size contributes to increasing measurement sensitivity.

The method for loading conjugate pad 2 with the test line detection reagent and the control line detection reagent can be any method. For example, the test line detection reagent and the control line detection reagent are mixed in a predetermined ratio; and the conjugate pad may be uniformly coated or sprayed with the mixture, or immersed in the mixture. The conjugate pad is then dried at an appropriate temperature in a thermostatic bath for a predetermined period of time, thereby loading the conjugate pad with the test line detection reagent and the control line detection reagent. The amount of the mixture applied is, although not particularly limited to, preferably 5 to 50 μL per centimeter of the line length. The concentration of the detection particles in the mixture is, although not particularly limited to, preferably 0.01 to 0.5 wt %, more preferably 0.02 to 0.2 wt %, and still more preferably 0.02 to 0.1 wt %. A concentration of less than 0.01 wt % may lead to insufficient capture and detection of Hb and HbA1c, lowering measurement sensitivity. A concentration of more than 0.5 wt %, on the other hand, does not help to increase measurement sensitivity, but increases cost. Drying is preferably performed after applying the mixture. The drying temperature is, although not particularly limited to, preferably 20° C. to 80° C., and more preferably 20° C. to 60° C. The drying time varies depending on the drying temperature, and is typically 5 to 120 minutes.

The linearly immobilized capture antibody that forms test line 6 on membrane 3 for use in the present invention is, although not particularly limited to, preferably anti-Hb antibody or anti-HbA1c antibody, and more preferably anti-Hb antibody. The anti-Hb antibody and anti-HbA1c antibody for use may be a commercially available product, or may be separately produced in accordance with a known method. The capture antibody may also be a monoclonal antibody or a polyclonal antibody, and may have any molecular size.

The linearly immobilized capture antibody that forms control line 7 on membrane 3 for use in the present invention is, although not particularly limited to, preferably an antibody for specifically capturing the labelling substance of the control line detection reagent. More specifically, when the labelling substance is biotin, the linearly immobilized capture antibody is anti-biotin antibody. When the labelling substance is digoxigenin, the linearly immobilized capture antibody is anti-digoxigenin antibody. The anti-biotin antibody and anti-digoxigenin antibody for use may be a commercially available product, or may be separately produced in accordance with a known method. The linearly immobilized capture antibody may also be a monoclonal antibody or a polyclonal antibody, and may have any molecular size.

The method for linearly immobilizing the capture antibody for forming the test line and the capture antibody for forming the control line on membrane 3 can be any method. For example, a predetermined amount of the capture antibody for forming the test line and a predetermined amount of the capture antibody for forming the control line are individually applied linearly to different areas; and dried at an appropriate temperature in a thermostatic bath for a predetermined period of time, thereby immobilizing the capture antibodies. The amount of the individual capture antibodies is, although not particularly limited to, preferably 0.1 to 2 μL per centimeter of the line length. The concentration of the individual capture antibodies applied is, although not particularly limited to, preferably 0.1 to 10 mg/mL, more preferably 0.2 to 5 mg/mL, and still more preferably 0.5 to 2 mg/mL. A low concentration may lead to insufficient capture and detection of Hb and HbA1c, decreasing measurement sensitivity. A high concentration, on the other hand, does not help to increase measurement sensitivity, but increases cost. Drying is preferably performed after applying the capture antibodies. The drying temperature is, although not particularly limited to, preferably 20° C. to 80° C., and more preferably 20° C. to 60° C. The drying time varies depending on the drying temperature, and is typically 5 to 120 minutes.

In the present invention, an immunochromatographic specimen can be prepared as follows. Membrane 3, prepared as described above, is adhered to the middle part of adhesive sheet 8, and conjugate pad 2 is then laminated onto membrane 3 with one end portion of membrane 3 partially covered by conjugate pad 2. Subsequently, sample pad 1 is laminated onto conjugate pad 2 so as to partially cover an end portion of conjugate pad 2, which is not the end portion that overlaps membrane 3. Absorbent pad 4 is then adhered onto the other end portion of membrane 3, with membrane 3 partially covered by absorbent pad 4. The resulting product is cut into strips of a predetermined width. Test line 6 and control line 7 may be prepared after test specimens are prepared, or before test specimens are prepared.

The immunochromatographic specimen may be accommodated in a suitable plastic housing case that has at least a first opening portion for dripping a measurement sample at a position above sample pad 1, and a second opening portion for measuring test line 6 and control line 7 at a position above membrane 3.

The method for measuring HbA1c (%) on a membrane using the measurement sample diluent and immunochromatographic specimen according to the present invention can be any method; an example of the method is as follows. First, a measurement sample is mixed with the measurement sample diluent in a predetermined dilution ratio to prepare a diluted measurement sample that can be developed. Subsequently, the diluted measurement sample is dropped onto sample pad 1; and the diluted measurement sample, due to capillary action, passes through sample pad 1 to develop into conjugate pad 2. At this stage, while dissolving the test line detection reagent and the control line detection reagent loaded on conjugate pad 2, the diluted measurement sample forms immunocomplexes of HbA1c in the diluted measurement sample and cellulose particles sensitized with anti-HbA1c antibody in the test line detection reagent. Hemoglobin molecules other than HbA1c in the diluted measurement sample (e.g., HbA0) do not form an immunocomplex with the test line detection reagent. Subsequently, the diluted measurement sample develops into membrane 3. When the diluted measurement sample reaches test line 6, the immunocomplexes are captured by the capture antibody that constitutes the test line (anti-Hb antibody) and accumulate, causing test line 6 to produce a color. Hemoglobin molecules other than HbA1c in the diluted measurement sample (e.g., HbA0) are also captured by the capture antibody that constitutes the test line (anti-Hb antibody), and accumulate. Thus, competitive capture between immunocomplexes and hemoglobin molecules other than HbA1c (e.g., HbA0) occurs on the test line, and the probability of capture depends on the proportion of HbA1c in the total Hb molecules (HbA1c (%)) in the measurement sample. More specifically, HbA1c (%) can be directly measured from the color intensity of the test line. Then, after the diluted measurement sample reaches control line 7, cellulose particles that have been sensitized with a blocking protein labelled with a labelling substance (biotin) in the control line detection reagent are captured by the capture antibody that constitutes the control line (anti-biotin antibody); and accumulate, causing control line 7 to produce a color. Finally, the diluted measurement sample is absorbed by absorbent pad 4.

HbA1c (%) may be directly measured based on the color intensity of the test line, or may be measured based on the corrected value obtained by dividing the color intensity of the test line by the color intensity of the control line, taking into consideration uneven flow of the diluted measurement sample.

In the present invention, the method for measuring the test line and control line of the immunochromatographic specimen can be any method; and can be performed using a commercially available immunochromatographic reader, or an immunochromatographic reader separately produced in accordance with a known method. The detection system for use can be any system, and examples include LED-FD, LED-CMOS, and LED-CCD.

EXAMPLES

Below, the present invention is described in detail with reference to Examples. The present invention is not limited to these Examples. HbA1c (%) in the Examples is an NGSP value in all cases.

Example 1

(1) Preparation of Test Line Detection Reagent for Measuring HbA1c

An 8.57 mg/mL anti-HbA1c monoclonal antibody (HbA1c Antibody, OAMA02329, produced by Aviva Systems Biology) was adjusted to 1.0 mg/mL with distilled water (Otsuka Distilled Water, produced by Otsuka Pharmaceutical Co., Ltd.). Subsequently, 100 µL of 1.0 wt % cellulose particles (NanoAct, registered trademark, BL2: dark navy, mean particle size: 365 nm, produced by Asahi Kasei Corporation), 900 µL of a 10 mM tris buffer (204-07885, produced by Wako Pure Chemical Industries, Ltd.) (pH 7.0), and 100 µL of the 1.0 mg/mL (0.1 wt %) anti-HbA1c monoclonal antibody were placed in a 15-mL centrifuge tube, and stirred with a vortex mixer. Subsequently, the mixture was placed in a low-temperature incubator adjusted to 37° C. (IN604, produced by Yamato Scientific Co., ltd.), and allowed to stand for 120 minutes. Subsequently, 12 mL of a blocking solution (pH 8.0) composed of 1.0 wt % casein (030-01505, produced by Wako Pure Chemical Industries, Ltd.) and a 100 mM boric acid buffer (021-02195, produced by Wako Pure Chemical Industries, Ltd.) was further added thereto; and the mixture was further allowed to stand for 60 minutes in a low-temperature incubator adjusted to 37° C. (IN604, produced by Yamato Scientific Co., Ltd.). Centrifugation was then performed at 10,000G at 25° C. for 15 minutes using a centrifugal separator (MX-307, produced by Tomy Seiko Co., Ltd.), a rack-in-rotor (TMA-300, produced by Tomy Seiko Co., Ltd.), and a rack (AR510-04, produced by Tomy Seiko Co., Ltd.) to allow the antibody-sensitized cellulose particles to settle out; and the supernatant was removed. Subsequently, 12 mL of a washing solution (pH 10.0) composed of a 50 mM boric acid buffer (021-02195, produced by Wako Pure Chemical Industries, Ltd.) was added, followed by treatment with a ultrasonic disperser (UH-50, produced by SMT Co., Ltd.) for 10 seconds. Centrifugation was then performed at 10,000G at 25° C. for 15 minutes using a centrifugal separator (MX-307, produced by Tomy Seiko Co., Ltd.), a rack-in-rotor (TMA-300, produced by Tomy Seiko Co., Ltd.), and a rack (AR510-04, produced by Tomy Seiko Co., Ltd.) to allow the antibody-sensitized cellulose particles to settle out; and the supernatant was removed. Subsequently, 2.0 mL of a coating solution (pH 9.2) composed of 15 wt % sucrose (196-00015, produced by Wako Pure Chemical Industries, Ltd.), 0.2 wt % casein (030-01505, produced by Wako Pure Chemical Industries, Ltd.), and a 62 mM boric acid buffer (021-02195, produced by Wako Pure Chemical Industries, Ltd.) was added; followed by treatment with a ultrasonic disperser (UH-50, produced by SMT Co., Ltd.) for 10 seconds, thereby obtaining a test line detection reagent for measuring HbA1c. The concentration of detection particles in the test line detection reagent for measuring HbA1c was 0.5 mg/mL (0.05 wt %), and the concentration of antibody was 0.05 mg/mL (0.005 wt %).

(2) Preparation of Control Line Detection Reagent for Measuring HbA1c 16 mg of D-biotin (04822-91, produced by Nacalai Tesque, Inc.) and 1000 µL of dimethyl sulfoxide (DMSO) (08904-14, produced by Nacalai Tesque, Inc.) were placed in a 1.5-mL microtube; and stirred with a vortex mixer, thereby obtaining a D-biotin solution. Subsequently, 20 mg of 1-ethyl-3-(3-dimethylaminopropyl)carbodiimide hydrochloride (EDC) (15022-86, produced by Nacalai Tesque, Inc.), 20 mg of N-hydroxysuccinimide (NHS) (18948-02, produced by Nacalai Tesque, Inc.), and 100 µL of distilled water (Otsuka distilled water, produced by Otsuka Pharmaceutical Co., Ltd.) were placed in a 1.5-mL microtube; and stirred with a vortex mixer, thereby obtaining an EDC-NHS solution. Subsequently, 100 µL of the D-biotin solution and 100 µL of the EDC-NHS solution were mixed, and then allowed to stand for 15 minutes in a low-temperature incubator (IN604, produced by Yamato Scientific Co., Ltd.) adjusted to 25° C.; thereby obtaining a D-biotin-EDC-NHS solution. Subsequently, 10 mg of a blocking peptide fragment (BPF) (BPF-301, produced by Toyobo Co., Ltd.) and 100 µL of distilled water (Otsuka distilled water, produced by Otsuka Pharmaceutical Co., Ltd.) were placed in a 1.5-mL microtube; and stirred with a vortex mixer, thereby obtaining a BPF solution. After 100 µL of the D-biotin-EDC-NHS solution and 100 µL of the BPF solution were mixed, the mixture was allowed to stand for 30 minutes in a low-temperature incubator (IN604, produced by Yamato Scientific Co., Ltd.) adjusted to 25° C.; thereby obtaining a D-biotin-BPF solution. Subsequently, 100 µL of 1.0 wt % cellulose particles (NanoAct, registered trademark, BL2:

dark navy, mean particle size: 365 nm, produced by Asahi Kasei Corporation), 900 μL of a 10 mM tris buffer (204-07885, produced by Wako Pure Chemical Industries, Ltd.) (pH 7.0), and 100 μL of the D-biotin-BPF solution were placed in a 15-mL centrifuge tube; and stirred with a vortex mixer. The mixture was then placed in a low-temperature incubator (IN604, produced by Yamato Scientific Co., Ltd.) adjusted to 37° C.; and allowed to stand for 120 minutes. Subsequently, 12 mL of a blocking solution (pH 8.0) composed of 1.0 wt % casein (030-01505, produced by Wako Pure Chemical Industries, Ltd.) and a 100 mM boric acid buffer (021-02195, produced by Wako Pure Chemical Industries, Ltd.) was added, and further allowed to stand for 60 minutes in a low-temperature incubator (IN604, produced by Yamato Scientific Co., Ltd.) adjusted to 37° C. Centrifugation was then performed at 10,000G at 25° C. for 15 minutes using a centrifugal separator (MX-307, produced by Tomy Seiko Co., Ltd.), a rack-in-rotor (TMA-300, produced by Tomy Seiko Co., Ltd.), and a rack (AR510-04, produced by Tomy Seiko Co., Ltd.) to allow the D-biotin-sensitized cellulose particles to settle out; and the supernatant was removed. Subsequently, 12 mL of a washing solution (pH 10.0) composed of a 50 mM boric acid buffer (021-02195, produced by Wako Pure Chemical Industries, Ltd.) was added, followed by treatment with a ultrasonic disperser (UH-50, produced by SMT Co., Ltd.) for 10 seconds. Centrifugation was then performed at 10,000G at 25° C. for 15 minutes using a centrifugal separator (MX-307, produced by Tomy Seiko Co., Ltd.), a rack-in-rotor (TMA-300, produced by Tomy Seiko Co., Ltd.), and a rack (AR510-04, produced by Tomy Seiko Co., Ltd.) to allow the D-biotin-sensitized cellulose particles to settle out; and the supernatant was removed. Subsequently, 2.0 mL of a coating solution (pH 9.2) composed of 15 wt % sucrose (196-00015, produced by Wako Pure Chemical Industries, Ltd.), 0.2 wt % casein (030-01505, produced by Wako Pure Chemical Industries, Ltd.), and a 62 mM boric acid buffer (021-02195, produced by Wako Pure Chemical Industries, Ltd.) was added, followed by treatment with a ultrasonic disperser (UH-50, produced by SMT Co., Ltd.) for 10 seconds; thereby obtaining a control line detection reagent for measuring HbA1c. The concentration of detection particles in the control line detection reagent for measuring HbA1c was 0.5 mg/mL (0.05 wt %), and the label introduction ratio of the blocking protein was 1:7.

(3) Preparation of Membrane Card for Measuring HbA1c

A 3.6 mg/mL anti-Hb monoclonal antibody (HBA1 Antibody, OAMA02326, produced by Aviva Systems Biology) was adjusted to 1.0 mg/mL with distilled water (Otsuka distilled water, produced by Otsuka Pharmaceutical Co., Ltd.), and a 1.0 mg/mL anti-biotin polyclonal antibody (Biotin Antibody, A150-111A, produced by Bethyl) was adjusted to 0.5 mg/mL with distilled water (Otsuka distilled water, produced by Otsuka Pharmaceutical Co., Ltd.). Subsequently, a membrane card (60 mm×300 mm)(Hi-Flow Plus 120 Membrane Cards, HF 120, produced by Millipore) composed of an adhesive tape part (20 mm×300 mm) located upstream, a membrane part (25 mm×300 mm) located in the middle, and an adhesive tape part (15 mm×300 mm) located downstream was coated, at a position 15 mm from upstream of the membrane part, with the 1.0 mg/mL anti-Hb monoclonal antibody in an amount of 1.0 μL/cm using a dispense platform (XYZ3060, produced by BioDot) and a BioJet nozzle (BHQHR-XYZ, produced by BioDot). The applied 1.0 mg/mL anti-Hb monoclonal antibody was dried for 30 minutes with a dryer adjusted to 45° C. (WFO-510, produced by Tokyo Rikakikai Co., Ltd.), thereby forming a test line with a line width of about 1 mm. The 0.5 mg/mL anti-biotin polyclonal antibody was further applied thereto in an amount of 1.0 μL/cm at a position 20 mm from upstream of the membrane part of the membrane card on which the test line was formed, using a dispense platform (XYZ3060, produced by BioDot) and a BioJet nozzle (BHQHR-XYZ, produced by BioDot); and dried for 30 minutes with a dryer adjusted to 45° C. (WFO-510, produced by Tokyo Rikakikai Co., Ltd.) to form a control line with a line width of about 1 mm, thereby obtaining a membrane card for measuring HbA1c.

(4) Preparation of Conjugate Pad for Measuring HbA1c

The test line detection reagent for measuring HbA1c and the control line detection reagent for measuring HbA1c were mixed in a mass ratio of 6:1. Note that when the concentration of particles in the test line detection reagent for measuring HbA1c is the same as the concentration of particles in the control line detection reagent for measuring HbA1c, these reagents may be mixed in a volume ratio of 6:1. Subsequently, the mixture was uniformly applied in an amount of 15 μL/cm onto the entire surface of a conjugate pad (10 mm×300 mm) (Glass Fiber Diagnostic Pad, GFDX001050, produced by Millipore) using a dispense platform (XYZ3060, produced by BioDot) and an air-jet nozzle (AJQHR-XYZ, produced by BioDot); and dried for 30 minutes with a dryer adjusted to 45° C. (WFO-510, produced by Tokyo Rikakikai Co., Ltd.), thereby obtaining a conjugate pad for measuring HbA1c.

(5) Preparation of Immunochromatographic Specimen for Measuring HbA1c

The conjugate pad for measuring HbA1c was adhered to the adhesive tape part (20 mm×300 mm) upstream on the membrane card for measuring HbA1c such that the conjugate pad overlaps the membrane part by 5 mm. Subsequently, a sample pad (20 mm×300 mm) (Cellulose Fiber Sample Pad, CFSP002000, produced by Millipore) was adhered upstream on the membrane card such that the sample pad overlaps the conjugate pad by 5 mm. An absorbent pad (20 mm×300 mm) (Cellulose Fiber Sample Pad, CFSP002000, produced by Millipore) was then further adhered to the adhesive tape part (15 mm×300 mm) downstream on the membrane card for measuring HbA1c such that the absorbent pad overlaps the membrane part by 2 mm. The resulting product was cut into strips (width: 4 mm, length: 63 mm) with a guillotine cutting module (CM5000, produced by BioDot), thereby obtaining immunochromatographic specimens for measuring HbA1c.

(6) Preparation of Measurement Sample Diluent

A bag of phosphate buffered saline powder (162-19321, produced by Wako Pure Chemical Industries, Ltd.), 2.0 g of polyoxyethylene (20) sorbitan monolaurate (Tween (registered trademark) 20, 166-21213, produced by Wako Pure Chemical Industries, Ltd.), 1.0 g of sodium dodecyl sulfate (SDS, 194-13985, produced by Wako Pure Chemical Industries, Ltd.), 0.2 g of sodium nitrite (199-02565, produced by Wako Pure Chemical Industries, Ltd.), and 0.2 g of sodium azide (199-11095, produced by Wako Pure Chemical Industries, Ltd.) were dissolved in 150 mL of distilled water (Otsuka distilled water, produced by Otsuka Pharmaceutical Co., Ltd.). The solution was then diluted with distilled water (Otsuka distilled water, produced by Otsuka Pharmaceutical Co., Ltd.) to 200 mL in a measuring cylinder; and transferred to a 500-mL glass bottle, thereby preparing a measurement sample diluent (50 mM PBS, 1.0 wt % Tween 20, 0.5 wt % SDS, 0.1 wt % sodium nitrite, 0.1 wt % sodium azide).

(7) Preparation of Diluted Sample

Samples for evaluating the measurement performance on HbA1c (QRM HbA1c 2007-1, produced by the Reference Material Institute for Clinical Chemistry Standards, five levels of L1 to L5), which are commercially available HbA1c standard substances, were individually diluted with the measurement sample diluent 500-fold, thereby obtaining diluted HbA1c samples L1 to L5. The percentage of HbA1c in the individual obtained samples was as follows: L1=5.01%, L2=5.65%, L3=7.35%, L4=9.51%, and L5=11.26%; and the concentration of Hb was 0.280 g/L in all of L1 to L5.

(8) Evaluation of Immunochromatographic Specimen for Measuring HbA1c: Evaluation of Sensitivity The immunochromatographic specimen for measuring HbA1c described above was placed on a horizontal table. Subsequently, 100 μL of a diluted HbA1c sample (L1 or L4), the mixing time for which was 10 seconds, was taken with a micropipette; and gently dropped onto a sample pad, followed by allowing the sample pad to stand at 25° C. for 10 minutes. The reflection absorption (mAbs) of the control line and the test line on the membrane was then measured using an immunochromatographic reader (C10060-10, measurement mode: Latex, Line, produced by Hamamatsu Photonics K.K.). This experimental operation was performed using diluted HbA1c samples L1 and L4 with N=10 for each sample (a total of 20 immunochromatographic specimens for measuring HbA1c was used). For an index of sensitivity, the difference between the average reflection absorption (mAbs) (N=10) of the test line of diluted HbA1c sample L4 and the average reflection absorption (mAbs) (N=10) of the test line of diluted HbA1c sample L1 ($\Delta$L4-L1) was calculated; and $\Delta$L4-L1$\geq$180 mAbs was rated as 3 points (excellent), 150 mAbs$\leq$$\Delta$L4-L1<180 mAbs as 2 points (good), 100 mAbs$\leq$$\Delta$L4-L1<150 mAbs as 1 point (average), and $\Delta$L4-L1<100 mAbs as 0 points (bad). The sensitivity of the immunochromatographic specimen for measuring HbA1c in Example 1 resulted in $\Delta$L4-L1=170 mAbs, rated as 2 points, indicating its high-sensitivity measurement capability.

(9) Evaluation of Immunochromatographic Specimen for Measuring HbA1c: Evaluation of Accuracy The immunochromatographic specimen for measuring HbA1c described above was placed on a horizontal table. Subsequently, 100 μL of a diluted HbA1c sample (L1 or L4), the mixing time for which was 10 seconds, was taken with a micropipette; and gently dropped onto a sample pad, followed by allowing the sample pad to stand at 25° C. for 10 minutes. The reflection absorption (mAbs) of the control line and the test line on the membrane was then measured using an immunochromatographic reader (C10060-10, measurement mode: Latex, Line, produced by Hamamatsu Photonics K.K.). This experimental operation was performed using diluted HbA1c samples L1 and L4 with N=10 for each sample (a total of 20 immunochromatographic specimens for measuring HbA1c was used). For an index of accuracy, corrected values (L1, L4) were calculated by dividing the reflection absorption (mAbs) of the test line of the diluted HbA1c sample (L1, L4) by the reflection absorption (mAbs) of the control line, and CV (%) in N=10 (L1, L4) for the obtained corrected values (L1, L4) was calculated. The average (CV (%)) between CV (L1) (%) and CV (L4) (%) was further calculated; CV<3% was rated as 3 points (excellent), 3%$\leq$CV<5% as 2 points (good), 5%$\leq$CV<10% as 1 point (average), and CV$\geq$10% as 0 points (bad). The accuracy of the immunochromatographic specimen for measuring HbA1c in Example 1 resulted in CV=3.3%, rated as 2 points, indicating its high-accuracy measurement capability.

(10) Evaluation of Immunochromatographic Specimen for Measuring HbA1c: Evaluation of Correlation with HPLC The immunochromatographic specimen for measuring HbA1c described above was placed on a horizontal table. Subsequently, 100 μL of a diluted HbA1c sample (L1 to L5), the mixing time for which was 10 seconds, was taken with a micropipette; and gently dropped onto a sample pad, followed by allowing the pad to stand at 25° C. for 10 minutes. The reflection absorption (mAbs) of the control line and the test line on the membrane was then measured using an immunochromatographic reader (C10060-10, measurement mode: Latex, Line, produced by Hamamatsu Photonics K.K.). This experimental operation was performed using diluted HbA1c samples L1 to L5 with N=10 for each sample (a total of 50 immunochromatographic specimens for measuring HbA1c was used). For an index for correlation, corrected values (L1 to L5) were calculated by dividing the reflection absorption (mAbs) of the test line by the reflection absorption (mAbs) of the control line of diluted HbA1c samples L1 to L5, and the Pearson correlation coefficient (r) between the obtained corrected values (L1 to L5) and HbA1c (%) of dilute HbA1c samples L1 to L5 (L1=5.01%, L2=5.65%, L3=7.35%, L4=9.51%, L5=11.26%) was calculated. Then, r$\geq$0.95 was rated as 3 points (excellent), 0.90$\leq$r<0.95 as 2 points (good), 0.85$\leq$r<0.90 as 1 point (average), and r<0.85 as 0 points (bad). The correlation of the immunochromatographic specimen for measuring HbA1c in Example 1 resulted in r=0.96 rated as 3 points, indicating its high correlation with HbA1c (%).

(11) Evaluation of Immunochromatographic Specimen for Measuring HbA1c: Evaluation of Mixing Time Dependency The immunochromatographic specimen for measuring HbA1c described above was placed on a horizontal table. Subsequently, 100 μL of a diluted HbA1c sample (L4), the mixing time for which was 10 seconds or 15 minutes, was taken with a micropipette; and gently dropped onto a sample pad, followed by allowing the sample to stand at 25° C. for 10 minutes. The reflection absorption (mAbs) of the control line and the test line on the membrane was then measured using an immunochromatographic reader (C10060-10, measurement mode: Latex, Line, produced by Hamamatsu Photonics K.K.). This experimental operation was performed using diluted HbA1c sample (L4), the mixing time for which was 10 seconds, and diluted HbA1c sample (L4), the mixing time for which was 15 minutes, with N=10 for each (a total of 20 immunochromatographic specimens for measuring HbA1c was used). For an index for mixing time dependency, the difference between the average reflection absorption (mAbs) of the test line of the diluted HbA1c sample (L4) (N=10), the mixing time for which was 15 minutes, and the average reflection absorption (mAbs) of the test line of the diluted HbA1c sample (L4) (N=10), the mixing time for which was 10 seconds, was calculated ($\Delta$15-10) (mAbs). Then, $\Delta$15-10$\leq$20 mAbs was rated as 3 points (excellent), 20 mAbs<$\Delta$15-10$\leq$100 mAbs rated as 2 points (good), 100 mAbs<$\Delta$15-10$\leq$200 mAbs rated as 1 point (average), and $\Delta$15-10>200 mAbs rated as 0 points (bad). The mixing time dependency of the immunochromatographic specimen for measuring HbA1c in Example 1 resulted in $\Delta$15-10=-10 mAbs, rated as 3 points; this indicates that there was no variation in reflection absorption of the test line due to the length of time required to mix the measurement sample and the measurement sample diluent, and to drop the mixture onto the immunochromatographic specimen for measuring HbA1c (mixing time).

Examples 2 to 27

Immunochromatographic specimens for measuring HbA1c were prepared and evaluated in the same manner as in Example 1, except that the formulation of the measurement sample diluent was changed. Table 1 illustrates the formulation of the measurement sample diluents and the obtained evaluation results. In Table 1, LDS indicates lithium dodecyl sulfate (121-02741, produced by Wako Pure Chemical Industries, Ltd.), Tween (registered trademark) 80 indicates polyoxyethylene (20) sorbitan monooleate (163-21625, produced by Wako Pure Chemical Industries, Ltd.), Triton X (registered trademark) 100 indicates polyoxyethylene (10) octylphenyl ether (160-24751, produced by Wako Pure Chemical Industries, Ltd.), NP-40 indicates Nonidet (registered trademark) P-40 (23640-65, produced by Nacalai Tesque, Inc.), $KNO_2$ indicates potassium nitrite (169-27325, produced by Wako Pure Chemical Industries, Ltd.), PIPES indicates a PIPES buffer (pH 7.5) (28104-16, produced by Nacalai Tesque, Inc.), and Tris indicates a tris buffer (pH 7.5) (204-07885, produced by Wako Pure Chemical Industries, Ltd.).

Examples 28 to 31

Immunochromatographic specimens for measuring HbA1c were prepared and evaluated in the same manner as in Example 1, except that in the step of preparing a diluted measurement sample, samples for evaluating the measurement performance on HbA1c (QRM HbA1c 2007-1, produced by Reference Material Institute for Clinical Chemistry Standards, five levels of L1 to L5), which are commercially available HbA1c standard substances, were individually diluted with the measurement sample diluent 50-fold (Example 28), 100-fold (Example 29), 1000-fold (Example 30), or 2000-fold (Example 31), instead of 500-fold. Table 1 illustrates the obtained evaluation results.

TABLE 1

| | Non-ionic Surfactant 1 | | Non-ionic Surfactant 2 | | Anionic Surfactant | | Buffer | | Oxidation Agent | | Azidation Agent | |
|---|---|---|---|---|---|---|---|---|---|---|---|---|
| | Type | Concentration (wt %) | Type | Concentration (wt %) | Type | Concentration (wt %) | Type | Concentration (mM) | Type | Concentration (wt %) | Type | Concentration (wt %) |
| Example 1 | Tween20 | 1.0 | — | — | SDS | 0.5 | PBS | 50 | NaNO2 | 0.1 | NaN3 | 0.1 |
| Example 2 | ↑ | ↑ | — | — | ↑ | ↑ | ↑ | ↑ | ↑ | ↑ | — | — |
| Example 3 | ↑ | ↑ | — | — | ↑ | ↑ | ↑ | ↑ | — | — | NaN3 | 0.1 |
| Example 4 | ↑ | ↑ | — | — | ↑ | ↑ | ↑ | ↑ | — | — | — | — |
| Example 5 | ↑ | ↑ | — | — | ↑ | 0.05 | ↑ | ↑ | NaNO2 | 0.1 | NaN3 | 0.1 |
| Example 6 | ↑ | ↑ | — | — | ↑ | 0.1 | ↑ | ↑ | ↑ | ↑ | ↑ | ↑ |
| Example 7 | ↑ | ↑ | — | — | ↑ | 1.0 | ↑ | ↑ | ↑ | ↑ | ↑ | ↑ |
| Example 8 | ↑ | ↑ | — | — | ↑ | 2.0 | ↑ | ↑ | ↑ | ↑ | ↑ | ↑ |
| Example 9 | ↑ | ↑ | — | — | LDS | 0.5 | ↑ | ↑ | ↑ | ↑ | ↑ | ↑ |
| Example 10 | ↑ | 0.05 | — | — | SDS | ↑ | ↑ | ↑ | ↑ | ↑ | ↑ | ↑ |
| Example 11 | ↑ | 0.1 | — | — | ↑ | ↑ | ↑ | ↑ | ↑ | ↑ | ↑ | ↑ |
| Example 12 | ↑ | 2.0 | — | — | ↑ | ↑ | ↑ | ↑ | ↑ | ↑ | ↑ | ↑ |
| Example 13 | ↑ | 3.0 | — | — | ↑ | ↑ | ↑ | ↑ | ↑ | ↑ | ↑ | ↑ |
| Example 14 | Tween80 | 1.0 | — | — | ↑ | ↑ | ↑ | ↑ | ↑ | ↑ | ↑ | ↑ |
| Example 15 | Tween20 | ↑ | TritonX100 | 0.1 | ↑ | ↑ | ↑ | ↑ | ↑ | ↑ | ↑ | ↑ |
| Example 16 | ↑ | ↑ | ↑ | 1.0 | ↑ | ↑ | ↑ | ↑ | ↑ | ↑ | ↑ | ↑ |
| Example 17 | ↑ | ↑ | ↑ | 2.0 | ↑ | ↑ | ↑ | ↑ | ↑ | ↑ | ↑ | ↑ |
| Example 18 | ↑ | ↑ | NP-40 | 1.0 | ↑ | ↑ | ↑ | ↑ | ↑ | ↑ | ↑ | ↑ |
| Example 19 | — | — | TritonX100 | ↑ | ↑ | ↑ | ↑ | ↑ | ↑ | ↑ | ↑ | ↑ |
| Example 20 | Tween20 | 1.0 | — | — | ↑ | ↑ | ↑ | ↑ | ↑ | 0.01 | ↑ | ↑ |
| Example 21 | ↑ | ↑ | — | — | ↑ | ↑ | ↑ | ↑ | KNO2 | 0.1 | ↑ | ↑ |
| Example 22 | ↑ | ↑ | — | — | ↑ | ↑ | ↑ | ↑ | NaNO2 | ↑ | ↑ | 0.01 |
| Example 23 | ↑ | ↑ | — | — | ↑ | ↑ | ↑ | ↑ | ↑ | ↑ | ↑ | 1.0 |
| Example 24 | ↑ | ↑ | — | — | ↑ | ↑ | ↑ | 10 | ↑ | ↑ | ↑ | 0.1 |
| Example 25 | ↑ | ↑ | — | — | ↑ | ↑ | ↑ | 100 | ↑ | ↑ | ↑ | ↑ |
| Example 26 | ↑ | ↑ | — | — | ↑ | ↑ | Tris | 10 | ↑ | ↑ | ↑ | ↑ |
| Example 27 | ↑ | ↑ | — | — | ↑ | ↑ | PIPES | ↑ | ↑ | ↑ | ↑ | ↑ |
| Example 28 | ↑ | ↑ | — | — | ↑ | ↑ | PBS | 50 | ↑ | ↑ | ↑ | ↑ |
| Example 29 | ↑ | ↑ | — | — | ↑ | ↑ | ↑ | ↑ | ↑ | ↑ | ↑ | ↑ |
| Example 30 | ↑ | ↑ | — | — | ↑ | ↑ | ↑ | ↑ | ↑ | ↑ | ↑ | ↑ |
| Example 31 | ↑ | ↑ | — | — | ↑ | ↑ | ↑ | ↑ | ↑ | ↑ | ↑ | ↑ |

| | Dilution Ratio | Reagent Loaded on Sample Pad | Sensitivity ΔL4-L1 | | Accuracy CV | | Correlation r | | Mixing Time Dependency Δ15-10 | |
|---|---|---|---|---|---|---|---|---|---|---|
| Example 1 | 500 | — | 170 mAbs | 2 | 3.3% | 2 | 0.96 | 3 | −10 mAbs | 3 |
| Example 2 | ↑ | — | 120 mAbs | 1 | 4.0% | 2 | 0.92 | 2 | 10 mAbs | 3 |
| Example 3 | ↑ | — | 190 mAbs | 3 | 4.5% | 2 | 0.91 | 2 | 30 mAbs | 2 |
| Example 4 | ↑ | — | 160 mAbs | 2 | 5.5% | 1 | 0.89 | 1 | 30 mAbs | 2 |
| Example 5 | ↑ | — | 100 mAbs | 1 | 4.5% | 2 | 0.90 | 2 | 60 mAbs | 2 |
| Example 6 | ↑ | — | 150 mAbs | 2 | 2.9% | 3 | 0.95 | 3 | 30 mAbs | 2 |
| Example 7 | ↑ | — | 160 mAbs | 2 | 2.7% | 3 | 0.96 | 3 | 10 mAbs | 3 |
| Example 8 | ↑ | — | 100 mAbs | 1 | 4.7% | 2 | 0.88 | 1 | −10 mAbs | 3 |

TABLE 1-continued

| | | | | | | | | | | |
|---|---|---|---|---|---|---|---|---|---|---|
| Example 9 | ↑ | — | 150 mAbs | 2 | 4.1% | 2 | 0.96 | 3 | 0 mAbs | 3 |
| Example 10 | ↑ | — | 200 mAbs | 3 | 8.1% | 1 | 0.89 | 1 | 10 mAbs | 3 |
| Example 11 | ↑ | — | 190 mAbs | 3 | 5.4% | 1 | 0.95 | 3 | 10 mAbs | 3 |
| Example 12 | ↑ | — | 160 mAbs | 2 | 3.2% | 2 | 0.96 | 3 | −10 mAbs | 3 |
| Example 13 | ↑ | — | 110 mAbs | 1 | 4.0% | 2 | 0.91 | 2 | 10 mAbs | 3 |
| Example 14 | ↑ | — | 160 mAbs | 2 | 4.3% | 2 | 0.95 | 3 | 10 mAbs | 3 |
| Example 15 | ↑ | — | 190 mAbs | 3 | 2.8% | 3 | 0.98 | 3 | −10 mAbs | 3 |
| Example 16 | ↑ | — | 200 mAbs | 3 | 2.2% | 3 | 0.99 | 3 | 10 mAbs | 3 |
| Example 17 | ↑ | — | 130 mAbs | 1 | 6.8% | 1 | 0.92 | 2 | −10 mAbs | 3 |
| Example 18 | ↑ | — | 220 mAbs | 3 | 2.4% | 3 | 0.99 | 3 | 10 mAbs | 3 |
| Example 19 | ↑ | — | 200 mAbs | 3 | 8.5% | 1 | 0.89 | 1 | 0 mAbs | 3 |
| Example 20 | ↑ | — | 180 mAbs | 3 | 3.9% | 2 | 0.94 | 2 | 20 mAbs | 3 |
| Example 21 | ↑ | — | 150 mAbs | 2 | 4.8% | 2 | 0.95 | 3 | 10 mAbs | 3 |
| Example 22 | ↑ | — | 160 mAbs | 2 | 3.7% | 2 | 0.95 | 3 | −10 mAbs | 3 |
| Example 23 | ↑ | — | 170 mAbs | 2 | 3.8% | 2 | 0.97 | 3 | 10 mAbs | 3 |
| Example 24 | ↑ | — | 170 mAbs | 2 | 4.4% | 2 | 0.95 | 3 | 10 mAbs | 3 |
| Example 25 | ↑ | — | 170 mAbs | 2 | 3.1% | 2 | 0.97 | 3 | −10 mAbs | 3 |
| Example 26 | ↑ | — | 180 mAbs | 3 | 4.2% | 2 | 0.96 | 3 | −10 mAbs | 3 |
| Example 27 | ↑ | — | 160 mAbs | 2 | 4.9% | 2 | 0.96 | 3 | 10 mAbs | 3 |
| Example 28 | 50 | — | 170 mAbs | 2 | 4.8% | 2 | 0.96 | 3 | 0 mAbs | 3 |
| Example 29 | 100 | — | 170 mAbs | 2 | 4.6% | 2 | 0.97 | 3 | −10 mAbs | 3 |
| Example 30 | 1000 | — | 160 mAbs | 2 | 4.3% | 2 | 0.95 | 3 | 0 mAbs | 3 |
| Example 31 | 2000 | — | 140 mAbs | 1 | 5.3% | 1 | 0.89 | 1 | 0 mAbs | 3 |

Comparative Examples 1 to 5

Immunochromatographic specimens for measuring HbA1c were prepared and evaluated in the same manner as in Example 1, except that the formulation of the measurement sample diluent was changed. Table 2 illustrates the formulation of the measurement sample diluents, and the obtained evaluation results.

As indicated in Table 2, in Comparative Example 1, which used a measurement sample diluent containing no surfactant, HbA1c (analyte) was not denatured, and HbA1c and detection particles sensitized with anti-HbA1c antibody were thus unable to form immunocomplexes on the conjugate pad; this resulted in a faint test line that could not be visually confirmed, indicating significantly low measurement sensitivity. In Comparative Example 1, accuracy, correlation, and mixing time dependency were not evaluated because the reflection absorption of the test line was near the lower detection limit.

In Comparative Example 2, which used a measurement sample diluent that contains no anionic surfactant (i.e., a measurement sample diluent that contains only Tween (registered trademark) 20, which is a non-ionic surfactant), HbA1c (analyte) was also not denatured, and HbA1c and detection particles sensitized with anti-HbA1c antibody were thus unable to form immunocomplexes on the conjugate pad; this resulted in a faint test line that could not be visually confirmed, indicating significantly low measurement sensitivity. In Comparative Example 2, accuracy, correlation, and mixing time dependency were not evaluated because the reflection absorption of the test line was near the lower detection limit.

In Comparative Examples 3 and 4, which used a measurement sample diluent that contains two types of non-ionic surfactants (Tween (registered trademark) 20 and Triton X (registered trademark) 100), it took time until HbA1c (analyte) was denatured; therefore, the reflection absorption of the test line varied considerably depending on the length of time required to mix the measurement sample and the measurement sample diluent and then to drop the mixture onto the immunochromatographic specimens for measuring HbA1c (mixing time). Additionally, due to the impact of mixing time dependency, measurement sensitivity and measurement accuracy immediately after mixing, assumed in a typical immunochromatography test, were significantly low.

In Comparative Example 5, which used a measurement sample diluent that contains only SDS (anionic surfactant), uneven development of the diluted measurement sample occurred downstream (in some cases, the sample did not develop downstream within a measurement time period), resulting in significantly low measurement accuracy.

Comparative Example 6

A bag of phosphate buffered saline powder (162-19321, produced by Wako Pure Chemical Industries, Ltd.) and 10 g of sodium dodecyl sulfate (SDS) (194-13985, produced by Wako Pure Chemical Industries, Ltd.) were dissolved in 150 mL of distilled water (Otsuka distilled water, produced by Otsuka Pharmaceutical Co., Ltd.), and diluted with distilled water (Otsuka distilled water) to 200 mL in a measuring cylinder; then transferred to a 500-mL glass bottle, thereby preparing a sample-pad coating solution (50 mM PBS, 5 wt % SDS). Subsequently, the sample-pad coating solution was uniformly applied in an amount of 30 μL/cm onto the entire surface of a sample pad (20 mm×300 mm) (Cellulose Fiber Sample Pads, CFSP002000, produced by Millipore) using a dispense platform (XYZ3060, produced by BioDot) and an air-jet nozzle (AJQHR-XYZ, produced by BioDot); and dried for 30 minutes with a dryer adjusted to 45° C. (WFO-510, produced by Tokyo Rikakikai Co., Ltd.), thereby obtaining a sample pad loaded with a surfactant. Then, an immunochromatographic specimen for measuring HbA1c was prepared and evaluated in the same manner as in Comparative Example 2, except that in the step of preparing an immunochromatographic specimen for measuring HbA1c, the sample pad loaded with a surfactant was used instead of the sample pad (20 mm×300 mm) (Cellulose Fiber Sample Pads, CFSP002000, produced by Millipore). Table 2 illustrates the formulation of the measurement sample diluent and the obtained evaluation results.

In Comparative Example 6, which used a measurement sample diluent that contains only Tween (registered trademark) 20 (non-ionic surfactant) and an immunochromatographic specimen having a sample pad loaded with SDS (anionic surfactant), the test line was faint, indicating low measurement sensitivity. The probable reason for this is that dissolution of SDS and denaturation of HbA1c did not completely proceed within the very short period of time during which the diluted measurement sample passed through the sample pad, and it was thus difficult for HbA1c and detection particles sensitized with anti-HbA1c antibody to form immunocomplexes on the conjugate pad. More specifically, this indicates that an anionic surfactant must be contained in a measurement sample diluent, rather than in a sample pad.

Comparative Example 7

A bag of phosphate buffered saline powder (162-19321, produced by Wako Pure Chemical Industries, Ltd.) and 20 g of polyoxyethylene (20) sorbitan monolaurate (Tween (registered trademark) 20, 166-21213, produced by Wako Pure Chemical Industries, Ltd.) were dissolved in 150 mL of distilled water (Otsuka distilled water, produced by Otsuka Pharmaceutical Co., Ltd.). The solution was then diluted with distilled water (Otsuka distilled water, produced by Otsuka Pharmaceutical Co., Ltd.) to 200 mL in a measuring cylinder; and transferred to a 500-mL glass bottle, thereby preparing a sample-pad coating solution (50 mM PBS, 10 wt % Tween 20). Subsequently, the sample-pad coating solution was uniformly applied in an amount of 30 μL/cm to the entire surface of a sample pad (20 mm×300 mm) (Cellulose Fiber Sample Pads, CFSP002000, produced by Millipore) using a dispense platform (XYZ3060, produced by BioDot) and an air-jet nozzle (AJQHR-XYZ, produced by BioDot); and dried for 30 minutes with a dryer adjusted to 45° C. (WFO-510, produced by Tokyo Rikakikai Co., Ltd.), thereby obtaining a sample pad loaded with a surfactant. An immunochromatographic specimen for measuring HbA1c was prepared and evaluated in the same manner as in Comparative Example 5, except that in the step of preparing an immunochromatographic specimen for measuring HbA1c, the sample pad loaded with a surfactant was used, instead of the sample pad (20 mm×300 mm) (Cellulose Fiber Sample Pads, CFSP002000, produced by Millipore). Table 2 illustrates the formulation of the measurement sample diluent and the evaluation results.

In Comparative Example 7, which used a measurement sample diluent that contains only SDS (anionic surfactant) and an immunochromatographic specimen having a sample pad loaded with Tween (registered trademark) 20 (non-ionic surfactant), measurement sensitivity was also low. The probable reason for this is that dissolution of Tween (registered trademark) did not completely proceed within the very short period of time during which the diluted measurement sample passed through the sample pad, and thus uneven development was not completely prevented. More specifically, this indicates that a non-ionic surfactant must be contained in a measurement sample diluent, rather than in a sample pad.

TABLE 2

| | Non-ionic Surfactant 1 | | Non-ionic Surfactant 2 | | Anionic Surfactant | | Buffer | | Oxidation Agent | | Azidation Agent | |
|---|---|---|---|---|---|---|---|---|---|---|---|---|
| | Type | Concentration (wt %) | Type | Concentration (wt %) | Type | Concentration (wt %) | Type | Concentration (mM) | Type | Concentration (wt %) | Type | Concentration (wt %) |
| Comparative Example 1 | — | — | — | — | — | — | PBS | 50 | NaNO2 | 0.1 | NaN3 | 0.1 |
| Comparative Example 2 | Tween20 | 1.0 | — | — | — | — | ↑ | ↑ | ↑ | ↑ | ↑ | ↑ |
| Comparative Example 3 | ↑ | ↑ | TritonX100 | 1.0 | — | — | ↑ | ↑ | ↑ | ↑ | ↑ | ↑ |
| Comparative Example 4 | ↑ | ↑ | ↑ | ↑ | — | — | ↑ | ↑ | — | — | ↑ | ↑ |
| Comparative Example 5 | — | — | — | — | SDS | 0.5 | ↑ | ↑ | NaNO2 | 0.1 | ↑ | ↑ |
| Comparative Example 6 | Tween20 | 1.0 | — | — | — | — | ↑ | ↑ | ↑ | ↑ | ↑ | ↑ |
| Comparative Example 7 | — | — | — | — | SDS | 0.5 | ↑ | ↑ | ↑ | ↑ | ↑ | ↑ |

| | Dilution Ratio | Reagent Loaded on Sample Pad | Sensitivity ΔL4-L1 | Accuracy CV | Correlation r | Mixing Time Dependency Δ15-10 |
|---|---|---|---|---|---|---|
| Comparative Example 1 | 500 | — | 10 mAbs | 0 | — | 0 | — | 0 | — | 0 |

TABLE 2-continued

| | | | | | | | | | | |
|---|---|---|---|---|---|---|---|---|---|---|
| Comparative Example 2 | ↑ | — | 10 mAbs | 0 | — | 0 | — | 0 | — | 0 |
| Comparative Example 3 | ↑ | — | 80 mAbs | 0 | 7.6% | 1 | 0.87 | 1 | 150 mAbs | 1 |
| Comparative Example 4 | ↑ | — | 110 mAbs | 1 | 8.8% | 1 | 0.82 | 0 | 230 mAbs | 0 |
| Comparative Example 5 | ↑ | — | 140 mAbs | 1 | 15% | 0 | 0.84 | 0 | 10 mAbs | 3 |
| Comparative Example 6 | ↑ | SDS | 50 mAbs | 0 | 7.2% | 1 | 0.88 | 1 | 80 mAbs | 2 |
| Comparative Example 7 | ↑ | Tween20 | 120 mAbs | 1 | 12% | 0 | 0.88 | 1 | −10 mAbs | 3 |

INDUSTRIAL APPLICABILITY

The present invention can provide an immunochromatographic specimen that enables the measurement of the proportion of HbA1c in the total Hb molecules in a measurement sample (HbA1c (%)), with high sensitivity, high accuracy, and high correlation with HPLC, without being affected by the length of time required to mix a measurement sample with a measurement sample diluent and to drop the mixture onto the immunochromatographic specimen.

DESCRIPTION OF REFERENCE NUMERALS

1: sample pad
2: conjugate pad
3: membrane
4: absorbent pad
5: backing sheet
6: test line
7: control line
8: adhesive sheet

The invention claimed is:

1. A measurement sample diluent for immunochromatography for quantifying hemoglobin A1c (%), which is the proportion of hemoglobin A1c in the total hemoglobin molecules in a measurement sample, the measurement sample diluent being an aqueous solution comprising
   an anionic surfactant,
   a non-ionic surfactant,
   an azidation agent, and
   a buffer.

2. The measurement sample diluent according to claim 1, wherein the anionic surfactant is an alkyl sulfate.

3. The measurement sample diluent according to claim 1, wherein the non-ionic surfactant is a polyoxyethylene sorbitan fatty acid ester.

4. The measurement sample diluent according to claim 1, wherein the non-ionic surfactant is a mixture of a polyoxyethylene sorbitan fatty acid ester and a polyoxyethylene alkyl phenyl ether.

5. The measurement sample diluent according to claim 1, comprising the anionic surfactant in an amount of 0.05 to 2.0 wt %, and the non-ionic surfactant in an amount of 0.05 to 3.0 wt %.

6. The measurement sample diluent according to claim 1, further comprising an oxidation agent.

7. The measurement sample diluent according to claim 6, wherein the oxidation agent is nitrite.

8. The measurement sample diluent according to claim 1 wherein the azidation agent is sodium azide.

9. A measurement kit for quantifying the proportion of hemoglobin A1c in the total hemoglobin molecules, the measurement kit comprising
   the measurement sample diluent of claim 1,
   an immunochromatographic specimen, and
   an immunochromatographic reader.

10. The measurement kit according to claim 9, wherein the immunochromatographic specimen comprises
   (1) a sample pad,
   (2) a conjugate pad loaded with a complex of an antibody for capturing any hemoglobin or hemoglobin A1c in the measurement sample and a cellulose particle,
   (3) a membrane on which an antibody for specifically capturing any hemoglobin or hemoglobin A1c in the measurement sample is linearly immobilized, and
   (4) an absorbent pad.

11. A method for quantifying the proportion of hemoglobin A1c in the total hemoglobin molecules in a measurement sample, using the measurement sample diluent of claim 1, the method comprising performing at least the following steps (i) to (iii) in this order:
   step (i): mixing the measurement sample and the measurement sample diluent in a volume ratio of 1:49 to 1:999 to dilute the measurement sample;
   step (ii): dropping the mixture of step (i) onto a sample pad on an immunochromatographic specimen; and
   step (iii): determining by colorimetry the proportion of hemoglobin A1c in the total hemoglobin molecules based on reflection absorption of a test line and reflection absorption of a control line on the immunochromatographic specimen.

12. The method according to claim 11, wherein the measurement sample and the measurement sample diluent are mixed in a volume ratio of 1:99 to 1:499 to dilute the measurement sample.

13. A method for quantifying the proportion of hemoglobin A1c in the total hemoglobin molecules in a measurement sample, using the measurement kit of claim 9, the method comprising performing at least the following steps (i) to (iii) in this order:
- step (i): mixing the measurement sample and the measurement sample diluent in a volume ratio of 1:49 to 1:999 to dilute the measurement sample;
- step (ii): dropping the mixture of step (i) onto the sample pad on the immunochromatographic specimen; and
- step (iii): determining by colorimetry the proportion of hemoglobin A1c in the total hemoglobin molecules based on reflection absorption of a test line and reflection absorption of a control line on the immunochromatographic specimen.

14. The method according to claim 13, wherein the measurement sample and the measurement sample diluent are mixed in a volume ratio of 1:99 to 1:499 to dilute the measurement sample.

* * * * *